US010066938B2

(12) United States Patent
Nomura et al.

(10) Patent No.: US 10,066,938 B2
(45) Date of Patent: Sep. 4, 2018

(54) ALTIMETER, ELECTRONIC TIMEPIECE, AND PROGRAM

(71) Applicant: SEIKO INSTRUMENTS INC., Chiba (JP)

(72) Inventors: Takayuki Nomura, Chiba (JP); Kazuhiro Koyama, Chiba (JP); Hiroshi Shimizu, Chiba (JP)

(73) Assignee: SEIKO INSTRUMENTS INC. (JP)

( * ) Notice: Subject to any disclaimer, the term of this patent is extended or adjusted under 35 U.S.C. 154(b) by 318 days.

(21) Appl. No.: 15/146,727

(22) Filed: May 4, 2016

(65) Prior Publication Data

US 2016/0327387 A1 Nov. 10, 2016

(30) Foreign Application Priority Data

May 8, 2015 (JP) .................................. 2015-095811
Feb. 5, 2016 (JP) .................................. 2016-021230

(51) Int. Cl.
| | |
|---|---|
| *G01C 5/00* | (2006.01) |
| *G01C 5/06* | (2006.01) |
| *A61B 5/00* | (2006.01) |
| *A63B 29/00* | (2006.01) |
| *A61B 5/11* | (2006.01) |

(52) U.S. Cl.
CPC .............. *G01C 5/06* (2013.01); *A61B 5/681* (2013.01); *A63B 29/00* (2013.01); *A61B 5/11* (2013.01); *A61B 2560/0242* (2013.01)

(58) Field of Classification Search
CPC .. G01C 5/06; A61B 5/11; A61B 5/681; A61B 2560/0242; A63B 29/00
See application file for complete search history.

(56) References Cited

U.S. PATENT DOCUMENTS

| | | | | |
|---|---|---|---|---|
| 4,835,716 A | * | 5/1989 | Tamaki ................... | B63C 11/32 368/14 |
| 5,646,857 A | * | 7/1997 | McBurney ............... | G01C 5/00 701/469 |
| 6,013,007 A | * | 1/2000 | Root ................... | A63B 24/0006 482/8 |
| 6,067,046 A | * | 5/2000 | Nichols ................. | G01C 15/00 342/357.31 |
| 6,381,540 B1 | * | 4/2002 | Beason .................... | G01C 5/06 342/120 |

(Continued)

OTHER PUBLICATIONS

Abstract, Publication No. 05-172569, Publication date Jul. 9, 1993.

(Continued)

*Primary Examiner* — David Bolduc
(74) *Attorney, Agent, or Firm* — Adams & Wilks

(57) ABSTRACT

An electronic timepiece includes a display unit, an altitude measurement unit that measures an altitude, a RAM that stores an ascent integrated altitude plan value which is a plan value of an ascent integrated altitude value, and a CPU that calculates the ascent integrated altitude value obtained by integrating an altitude variation amount during an ascent, based on an altitude measured by the altitude measurement unit, that calculates an ascent achievement ratio which is an achievement ratio of the ascent integrated altitude value with respect to the ascent integrated altitude plan value, and that causes the display unit to display the ascent achievement ratio.

13 Claims, 8 Drawing Sheets

(56) References Cited

U.S. PATENT DOCUMENTS

| | | | | |
|---|---|---|---|---|
| 6,502,032 B1* | 12/2002 | Newman | G09B 21/003 | 345/156 |
| 6,522,298 B1* | 2/2003 | Burgett | G01C 5/06 | 342/357.25 |
| 6,735,542 B1* | 5/2004 | Burgett | G01C 5/06 | 701/4 |
| 6,798,378 B1* | 9/2004 | Walters | G01C 5/00 | 342/357.57 |
| 6,813,582 B2* | 11/2004 | Levi | G01C 21/12 | 701/495 |
| 6,862,525 B1* | 3/2005 | Beason | G01C 21/20 | 701/454 |
| 7,057,551 B1* | 6/2006 | Vogt | A63B 69/0028 | 342/357.57 |
| 7,398,151 B1* | 7/2008 | Burrell | A63B 24/0062 | 342/357.75 |
| 7,433,805 B2* | 10/2008 | Vock | G01P 3/50 | 235/444 |
| 7,534,206 B1* | 5/2009 | Lovitt | A61B 5/02438 | 600/300 |
| 8,688,374 B1* | 4/2014 | Boerger | G01S 19/19 | 701/487 |
| 8,781,730 B2* | 7/2014 | Downey | G01C 21/3676 | 340/995.11 |
| 9,500,478 B2* | 11/2016 | Shin | G01C 5/06 | |
| 2005/0107216 A1* | 5/2005 | Lee | A63B 24/0084 | 482/8 |
| 2006/0157517 A1* | 7/2006 | Fiske | B05C 5/001 | 222/504 |
| 2007/0067137 A1* | 3/2007 | Ohkubo | G01C 21/28 | 702/142 |
| 2008/0082254 A1* | 4/2008 | Huhtala | G01C 21/00 | 701/533 |
| 2008/0096493 A1* | 4/2008 | Kerwood | A63B 29/00 | 455/90.2 |
| 2010/0170337 A1* | 7/2010 | Ahlstrom | G01L 19/08 | 73/384 |
| 2010/0331145 A1* | 12/2010 | Lakovic | G04F 10/00 | 482/8 |
| 2011/0106449 A1* | 5/2011 | Chowdhary | G01C 21/005 | 701/472 |
| 2011/0144910 A1* | 6/2011 | Sakashita | G01C 5/06 | 701/469 |
| 2012/0285242 A1* | 11/2012 | Miyake | G01W 1/02 | 73/384 |
| 2012/0290253 A1* | 11/2012 | Barrett | G01C 5/06 | 702/150 |
| 2013/0133421 A1* | 5/2013 | Katz | G01C 5/06 | 73/490 |
| 2013/0204567 A1* | 8/2013 | Nieminen | G01C 5/00 | 702/94 |
| 2013/0257650 A1 | 10/2013 | Miyake | 342/357.31 | |
| 2014/0039839 A1* | 2/2014 | Yuen | G06K 9/22 | 702/189 |
| 2014/0174958 A1* | 6/2014 | Martinez | G06F 15/00 | 206/37 |
| 2014/0278139 A1* | 9/2014 | Hong | A61B 5/4866 | 702/19 |
| 2014/0278220 A1* | 9/2014 | Yuen | G01B 21/16 | 702/150 |
| 2015/0192414 A1* | 7/2015 | Das | G01C 5/06 | 73/384 |
| 2017/0056724 A1* | 3/2017 | Baker | G09B 19/0038 | |

OTHER PUBLICATIONS

Abstract, Publication No. 2008-082909, Publication date Apr. 10, 2008.

* cited by examiner

105 DISPLAY UNIT
103 FREQUENCY DIVISION CIRCUIT
102 OSCILLATION CIRCUIT
109 RADIO COMMUNICATION MEANS
104 KEY INPUT MEANS
108 ALTITUDE MEASUREMENT UNIT
106 BATTERY
107 ATMOSPHERIC PRESSURE MEASUREMENT UNIT

S101 MEASURE ALTITUDE
S102 CALCULATE DIFFERENCE BETWEEN CURRENT MEASUREMENT VALUE
     AND PREVIOUS MEASUREMENT VALUE
S103 IS CALCULATION RESULT CORRECT?
S104 ADD DIFFERENCE TO ASCENT INTEGRATED ALTITUDE VALUE
S106 CALCULATE ACHIEVEMENT RATIO
S107 CALCULATE ASCENT SPEED
S108 UPDATE DISPLAY

S105 ADD ABSOLUTE VALUE OF DIFFERENCE
     TO DESCENT INTEGRATED ALTITUDE VALUE

ALTIMETER, ELECTRONIC TIMEPIECE, AND PROGRAM

BACKGROUND OF THE INVENTION

Field of the Invention

The present invention relates to an altimeter, an electronic timepiece, and a program.

Background Art

A technique for obtaining an altitude variation amount from movement start until the current time is known. For example, Japanese Patent No. 5652418 discloses a technique in which if a reversed atmospheric pressure variation direction is detected, altitude information is acquired by radio communication means so as to acquire an ascent integrated altitude value obtained by integrating an altitude variation amount during an ascent and a descent integrated altitude value obtained by integrating an altitude variation amount during a descent. In addition, JP-A-2008-82909 discloses a technique in which if "measured altitude-base altitude =alarm altitude" is satisfied, a buzzer is driven so as to acoustically notify that an altitude has reached the alarm altitude. In addition, JP-A-5-172569 discloses a technique in which current altitudes are sequentially detected at predetermined timings and a difference is calculated between the current altitude and the previous altitude so as to accumulate at least one difference in each altitude variation direction.

However, although each technique disclosed in Japanese Patent No. 5652418, JP-A-2008-82909, and JP-A-5-172569 can obtain the altitude variation amount from the movement start to the current time, there is a problem in that it is not possible to know what ratio of a total plan is achieved. In addition, in some cases, the altitude variation amount from the movement start until the current time is different from an altitude difference caused by an actual movement. Consequently, even if the variation amount is recognized, a user does not actually feel the variation amount. In addition, in order to know an achievement ratio thereof, the user has to calculate the variation amount by comparing the total plan and the current value with each other, thereby causing the user to feel cumbersome. For example, in a case of a mountain climbing, an ascent/descent achievement ratio at a certain time becomes a criterion in determining whether to continue or to discontinue the mountain climbing. However, a mountaineer has to calculate the achievement ratio. Thus, the mountaineer is less likely to immediately determine whether to continue or to discontinue the mountain climbing.

SUMMARY OF THE INVENTION

Therefore, the present invention is made in view of the above-described circumstances, and an object thereof is to provide an altimeter, an electronic timepiece, and a program by which a user can realistically know an ascent/descent achievement ratio with respect to a plan.

According to an aspect of the present invention, there is provided an altimeter including a display unit, an altitude measurement unit that measures an altitude, an altitude integration unit that calculates an ascent integrated altitude value obtained by integrating an altitude variation amount during an ascent, based on the altitude measured by the altitude measurement unit, a storage unit that stores an ascent integrated altitude plan value which is a plan value of the ascent integrated altitude value, an achievement ratio calculation unit that calculates an ascent achievement ratio which is an achievement ratio of the ascent integrated altitude value with respect to the ascent integrated altitude plan value, and a display control unit that causes the display unit to display the ascent achievement ratio.

In the aspect, the altitude integration unit may calculate a descent integrated altitude value obtained by integrating an altitude variation amount during a descent, based on the altitude measured by the altitude measurement unit. The storage unit may store a descent integrated altitude plan value which is a plan value of the descent integrated altitude value. The achievement ratio calculation unit may calculate a descent achievement ratio which is an achievement ratio of the descent integrated altitude value with respect to the descent integrated altitude plan value. The display control unit may cause the display unit to display the descent achievement ratio.

In the aspect, the altimeter may further include an input unit that receives an input. If the input unit receives a predetermined input, the achievement ratio calculation unit may set the integrated altitude plan value, based on the integrated altitude value previously calculated by the altitude integration unit, and may calculate the achievement ratio, based on the set integrated altitude plan value.

In the aspect, the storage unit may store an absolute value of the ascent integrated altitude value obtained when the predetermined input is received, as the descent integrated altitude plan value. The altitude integration unit may calculate the descent integrated altitude value based on the altitude obtained when the predetermined input is received. The achievement ratio calculation unit may calculate the descent achievement ratio which is an achievement ratio of the descent integrated altitude value with respect to the descent integrated altitude plan value.

In the aspect, the altimeter may further include an input unit that receives an input. If the input unit receives a predetermined input, the achievement ratio calculation unit may cause the storage unit to store a value obtained by adding an absolute value of the ascent integrated altitude value and an absolute value of the descent integrated altitude value which are obtained when the predetermined input is received, as the ascent integrated altitude plan value and the descent integrated altitude plan value, may calculate the ascent achievement ratio, based on the ascent integrated altitude plan value stored in the storage unit, and may calculate the descent achievement ratio, based on the descent integrated altitude plan value stored in the storage unit.

In the aspect, the altimeter may further include an input unit that receives an input. If the input unit receives a predetermined input, the altitude integration unit may calculate the ascent integrated altitude value by deducting an absolute value of the descent integrated altitude value obtained after the predetermined input is received from an absolute value of the ascent integrated altitude value obtained when the predetermined input is received, and may calculate the descent integrated altitude value by deducting an absolute value of the ascent integrated altitude value obtained after the predetermined input is received from an absolute value of the descent integrated altitude value obtained when the predetermined input is received.

In the aspect, if the input unit receives the predetermined input, the display control unit may change a display method of the achievement ratio.

In the aspect, the display control unit may cause the display unit to display at least one of altitude measured by the altitude measurement unit, speed based on the altitude variation amount, and a time, together with the achievement ratio.

In the aspect, the display control unit may cause the display unit to display at least one of altitude measured by the altitude measurement unit, speed relating to the altitude, and a time, together with the ascent achievement ratio and the descent achievement ratio.

In the aspect, the display control unit may cause the display unit to display the achievement ratio which can visibly identify a size, based on a display area, and may display the achievement ratio so that a direction in which the display area for displaying the ascent achievement ratio increases and a direction in which the display area for displaying the descent achievement ratio increases are opposite to each other in the display unit.

In the aspect, the altimeter may further include a solar cell that generates power required for display of the display unit. The solar cell may generate the power by using light received while the altitude measurement unit measures the altitude.

According to another aspect of the present invention, there is provided an electronic timepiece including any one of the above-described altimeters and a clocking function. The display control unit enables the display unit to display a time clocked by the clocking function.

According to still another aspect of the present invention, there is provided a program that causes a computer of an altimeter to execute a process including an altitude measurement step of measuring an altitude, an altitude integration step of calculating an ascent integrated altitude value obtained by integrating an altitude variation amount during an ascent, based on the altitude measured in the altitude measurement step, an achievement ratio calculation step of calculating an ascent achievement ratio which is an achievement ratio of the ascent integrated altitude value with respect to an ascent integrated altitude plan value which is a plan value of the ascent integrated altitude value, and a display control step of causing a display unit to display the ascent achievement ratio.

According to the present invention, an electronic timepiece includes a display unit, an altitude measurement unit that measures an altitude, a storage unit that stores an ascent integrated altitude plan value which is a plan value of the ascent integrated altitude value, an altitude integration unit, an achievement ratio calculation unit, and a display control unit. The altitude integration unit calculates the ascent integrated altitude value obtained by integrating an altitude variation amount during an ascent, based on the altitude measured by the altitude measurement unit. The achievement ratio calculation unit calculates an ascent achievement ratio which is an achievement ratio of the ascent integrated altitude value with respect to the ascent integrated altitude plan value. The display control unit causes the display unit to display the ascent achievement ratio. According to this configuration, a user can easily recognize an ascent/descent achievement ratio with respect to a plan.

DETAILED DESCRIPTION OF THE INVENTION

Hereinafter, embodiments according to the present invention will be described with reference to the drawings.

First Embodiment

Figure 1:
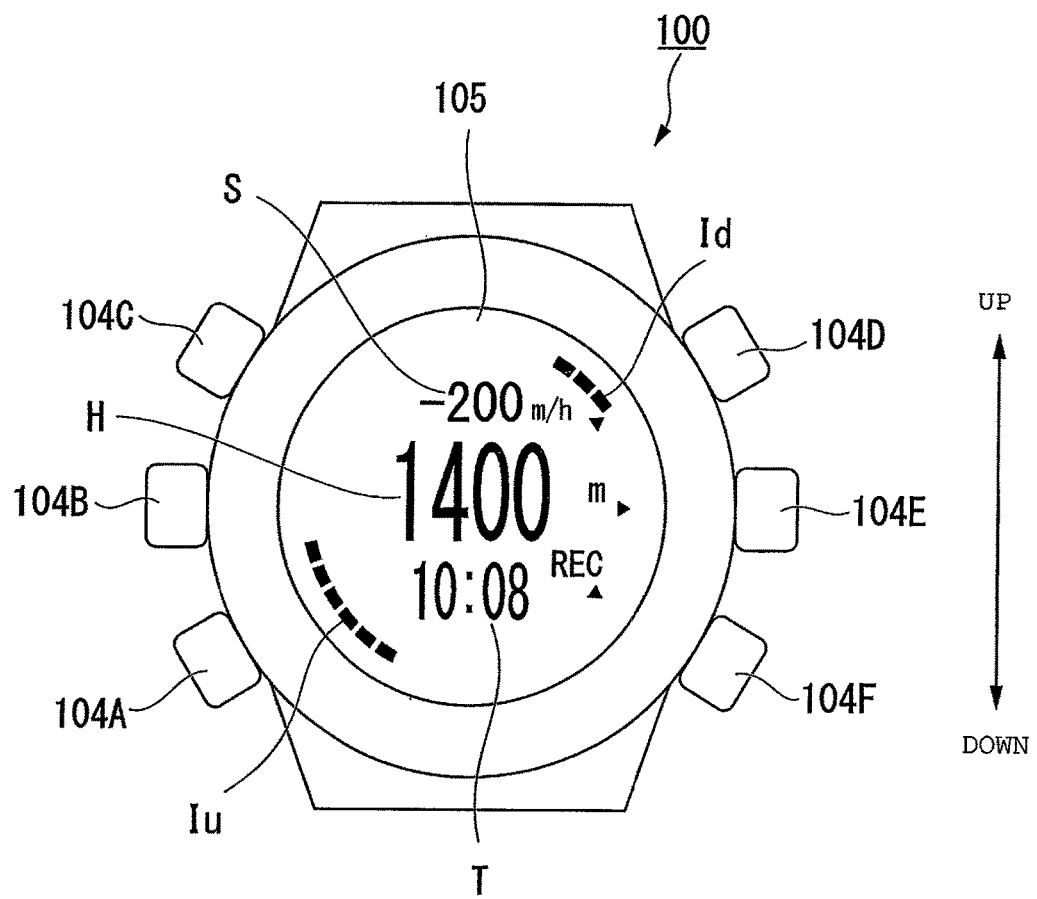
FIG. 1 is a front view illustrating an external configuration of an electronic timepiece according to a first embodiment of the present invention.

First, a first embodiment according to the present invention will be described. In the present embodiment, as an example of an electronic device (altimeter), an electronic time piece will be described. FIG. 1 is a front view illustrating an external configuration of an electronic timepiece 100 according to the present embodiment. The electronic timepiece 100 is an electronic timepiece provided with an altitude measurement function. As illustrated, the electronic timepiece 100 includes a plurality of (six in the present embodiment) key input means 104A to 104F and a display unit 105.

The key input means 104A to 104F (input units) receive an operation input. The input unit receiving the operation input may be configured to include the plurality of key input means 104, or may be configured to include single key input means 104.

The display unit 105 is a liquid crystal display or a segment display, and displays information. The display unit 105 displays ascent speed S, an altitude H, a time T, an indicator Iu for indicating an ascent achievement ratio, and an indicator Id for indicating a descent achievement ratio. The ascent speed S is a speed at which the altitude ascends (unit is m/h), and is a value calculated in such a way that an altitude variation amount is divided by the time. The altitude H is a current altitude (unit is m). The time T is a current time. The ascent achievement ratio is an achievement ratio (unit is %) of an ascent integrated altitude value with respect to an ascent integrated altitude plan value. The ascent integrated altitude value is a value obtained by integrating the altitude variation amount during an ascent from when a movement starts until the current time. The ascent integrated altitude plan value is a plan value of the ascent integrated altitude value. The descent achievement ratio is an achievement ratio of a descent integrated altitude value with respect to a descent integrated altitude plan value. The descent integrated altitude value is a value obtained by integrating the altitude variation amount during a descent from when a movement starts until the current time. The descent integrated altitude plan value is a plan value of the descent integrated altitude value.

The indicator Iu and the indicator Id indicate the ascent achievement ratio or the descent achievement ratio by using a shape whose size can be visually identified based on a display area. Specifically, in the indicator Iu and the indicator Id, if the display area becomes wider, the ascent achievement ratio or the descent achievement ratio increases, and if the display area becomes narrower, the ascent achievement ratio or the descent achievement ratio decreases. In addition, in the indicator Iu, a lower side indicates 0%, and un upper side indicates 100%. That is, if the ascent achievement ratio increases, the display area of the indicator Iu increases sequentially from the lower side to the upper side. In addition, in the indicator Id, the upper side indicates 0%, and the lower side indicates 100%. That is, if the descent achievement ratio increases, the display area of the indicator Id increases sequentially from the upper side to the lower side. In other words, a direction in which the display area indicating the ascent achievement ratio increases and a direction in which the display area indicating the descent achievement ratio increases are opposite to each other. In this manner, a user actually feels a change in indicator display, when he or she performs an ascending or descending operation, thereby allowing the user to feel improved convenience as a user interface.

Figure 2:
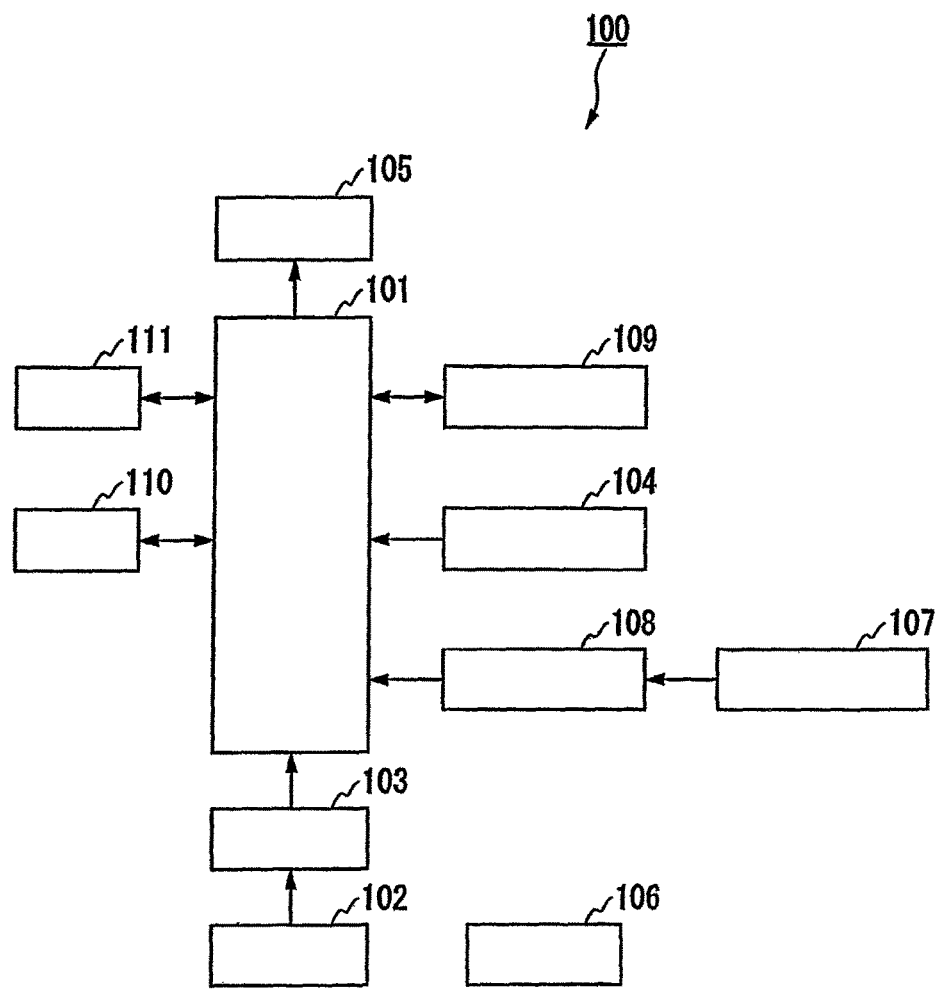
FIG. 2 is a block diagram illustrating a configuration of the electronic timepiece according to the first embodiment of the present invention.

FIG. 2 is a block diagram illustrating a configuration of the electronic timepiece 100 according to the present embodiment. The electronic timepiece 100 includes a central processing unit (CPU) 101 (an altitude integration unit, an achievement ratio calculation unit, and a display control unit), an oscillation circuit 102, a frequency division circuit 103, the key input means 104, the display unit 105, a battery (solar cell) 106, an atmospheric pressure measurement unit 107, an altitude measurement unit 108, radio communication means 109, a random access memory (RAM) 110 (a storage unit), and a read only memory (ROM) 111.

The CPU 101 controls each unit included in the electronic timepiece 100. Based on an altitude measured by the altitude measurement unit 108, the CPU 101 calculates an ascent integrated altitude value obtained by integrating an altitude variation amount during an ascent and a descent integrated altitude value obtained by integrating an altitude variation amount during a descent. Subsequently, the CPU 101 reads an ascent integrated altitude plan value which is a plan value of the ascent integrated altitude value and a descent integrated altitude plan value which is a plan value of the descent integrated altitude value from the RAM 110, and calculates an ascent achievement ratio which is an achievement ratio of the ascent integrated altitude value with respect to the read ascent integrated altitude plan value and a descent achievement ratio which is an achievement ratio of the descent integrated altitude value with respect to the read descent integrated altitude plan value.

The CPU 101 includes a clocking function for clocking a current time, based on a measurement signal input from the frequency division circuit 103. The CPU 101 calculates ascent speed, based on the altitude measured by the altitude measurement unit 108 and the clocked time.

The CPU 101 causes the display unit 105 to display the calculated ascent speed, the altitude measured by the altitude measurement unit 108, the clocked current time, the calculated ascent achievement ratio, and the calculated descent achievement ratio. In this case, the CPU 101 displays the ascent achievement ratio and the descent achievement ratio by using a predetermined display area (indicator) having a visibly identifiable figure.

If the key input means 104 receives a predetermined input indicating that a user returns, the CPU 101 sets the previously calculated ascent integrated altitude value in the descent integrated altitude plan value, sets the previously calculated descent integrated altitude value in the ascent integrated altitude plan value, and initializes the ascent integrated altitude value and the descent integrated altitude value to zero. For example, the CPU 101 writes an absolute value of the ascent integrated altitude value obtained when the predetermined input is received, on the RAM 110 as the descent integrated altitude plan value. The CPU 101 writes an absolute value of the descent integrated altitude value obtained when the predetermined input is received, on the RAM 110 as the ascent integrated altitude plan value. Then, the CPU 101 calculates the ascent integrated altitude value and the descent integrated altitude value which are based on the altitude obtained when the predetermined input is received. Then, the CPU 101 calculates the ascent achievement ratio which is the achievement ratio of the ascent integrated altitude value with respect to the set ascent integrated altitude plan value and the descent achievement ratio which is the achievement ratio of the descent integrated altitude value with respect to the set descent integrated altitude plan value, and causes the display unit 105 to display both of these.

The oscillation circuit 102 generates an oscillation signal having a predetermined frequency (for example, 32,768 Hz), and outputs the signal to the frequency division circuit 103. The frequency division circuit 103 divides the frequency of the oscillation signal input from the oscillation circuit 102, generates a measurement signal serving as a measurement reference, and outputs the generated measurement signal to the CPU 101. The key input means 104 (104A to 104F) receives an operation input. The battery 106 supplies power for operating to each unit included in the electronic timepiece 100. For example, the battery 106 includes a solar cell for generating the power by using light received from the outside of the electronic timepiece 100 during a period while the altitude measurement unit 108 measures the altitude. Then, the battery 106 charges a rechargeable secondary battery with the power generated by the solar cell, thereby supplying the power for operating each unit, when necessary. For example, the battery 106 can supply the power required for display to the display unit 105. Since the battery 106 is the solar cell, a situation which needs battery replacement is less likely to occur during an ascent or during a descent. Therefore, it is possible to stably ensure altitude measurement in the altitude measurement unit 108 and an operation for displaying the achievement ratio in the display unit 105 during the ascent or during the descent.

For example, the atmospheric pressure measurement unit 107 is an atmospheric pressure sensor, which measures atmospheric pressure and outputs the measured atmospheric pressure to the altitude measurement unit 108. Based on the atmospheric pressure input from the atmospheric pressure measurement unit 107, the altitude measurement unit 108 measures the altitude, and outputs the measured altitude to the CPU 101. The atmospheric pressure measurement unit 107 and the altitude measurement unit 108 configure an altimeter for measuring the altitude. The radio communication means 109 communicates with other devices by using radio communication such as a radio local area network (LAN) and Bluetooth (registered trademark).

The RAM 110 stores data used for each unit in the electronic timepiece 100. For example, the RAM 110 stores the ascent integrated altitude plan value and the descent integrated altitude plan value. The ROM 111 stores an operation program executed by the CPU 101 in advance. The operation program is read when the CPU 101 is driven.

Figure 3:
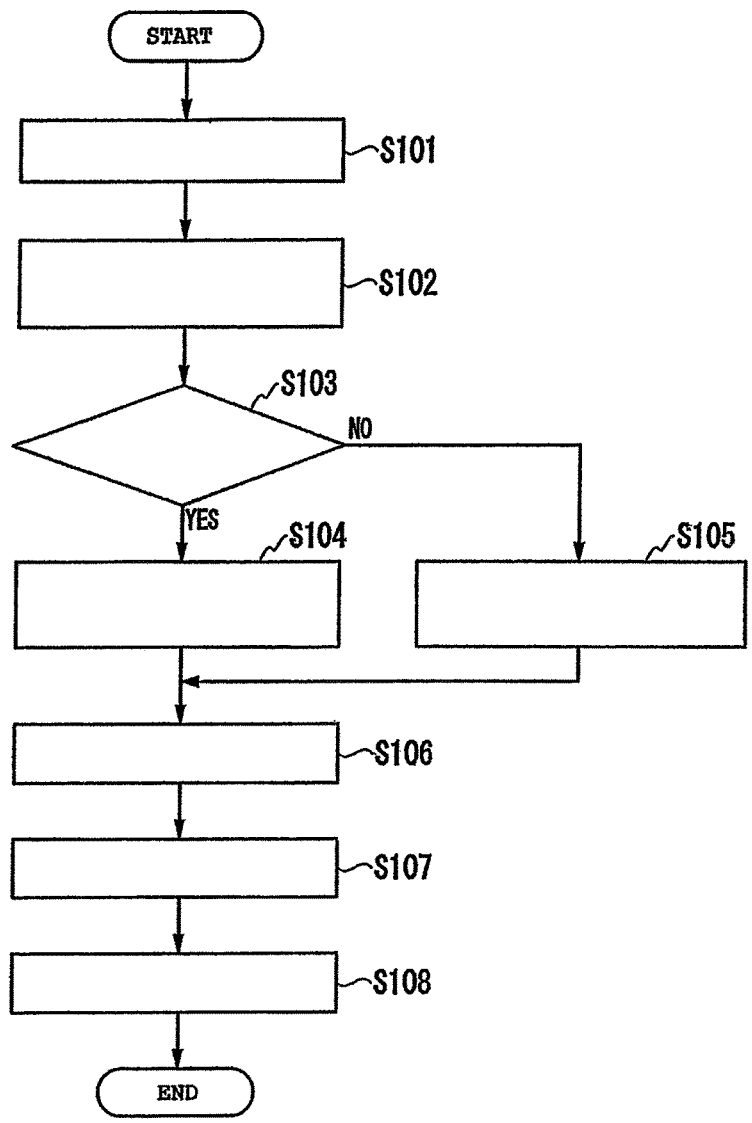
FIG. 3 is a flowchart illustrating a processing procedure in an achievement ratio display process performed by the electronic timepiece according to the first embodiment of the present invention.

Next, an achievement ratio display process will be described in which the electronic timepiece 100 according to the present embodiment displays the ascent achievement ratio and the descent achievement ratio. FIG. 3 is a flowchart illustrating a processing procedure in the achievement ratio display process performed by the electronic timepiece 100 according to the present embodiment. If the key input means 104 receives an input of mountain climbing log start indicating mountain climbing start, the electronic timepiece 100 repeatedly performs the illustrated achievement ratio display process at every predetermined time (for example, every 10 seconds).

(Step S101) The CPU 101 acquires a measurement altitude measured by the altitude measurement unit 108. Thereafter, the process proceeds to Step S102.

(Step S102) The CPU 101 calculates a differential value by deducting the previously acquired measurement altitude from the currently acquired measurement altitude. Thereafter, the process proceeds to Step S103.

(Step S103) The CPU 101 determines whether or not the calculated differential value is a positive value. In a case where the CPU 101 determines that the differential value is the positive value, the process proceeds to Step S104. In a case where the CPU 101 determines that the differential value is not the positive value, the process proceeds to Step S105.

(Step S104) The CPU 101 adds the calculated differential value to the ascent integrated altitude value. An initial value of the ascent integrated altitude value is zero. Thereafter, the process proceeds to Step S106.

(Step S105) The CPU 101 adds an absolute value of the calculated differential value to the descent integrated altitude value. An initial value of the descent integrated altitude value is zero. Thereafter, the process proceeds to Step S106.

(Step S106) The CPU 101 calculates the ascent achievement ratio, based on the ascent integrated altitude value and the ascent integrated altitude plan value. Specifically, the CPU 101 calculates the ascent achievement ratio by using "ascent integrated altitude value/ascent integrated altitude plan value×100". The CPU 101 calculates the descent achievement ratio, based on the descent integrated altitude value and the descent integrated altitude plan value. Specifically, the CPU 101 calculates the descent achievement ratio by using "descent integrated altitude value/descent integrated altitude plan value×100". Thereafter, the process proceeds to Step S107.

(Step S107) The CPU 101 calculates ascent speed in such a way that the differential value is divided by a time elapsed from when the previous altitude is measured. Thereafter, the process proceeds to Step S108.

(Step S108) The CPU 101 updates the display of the display unit 105. Specifically, the CPU 101 causes the display unit 105 to display the calculated ascent speed, the measured altitude, the clocked current time, the indicator for indicating the calculated ascent achievement ratio, and the indicator for indicating the calculated descent achievement ratio.

Figure 4:
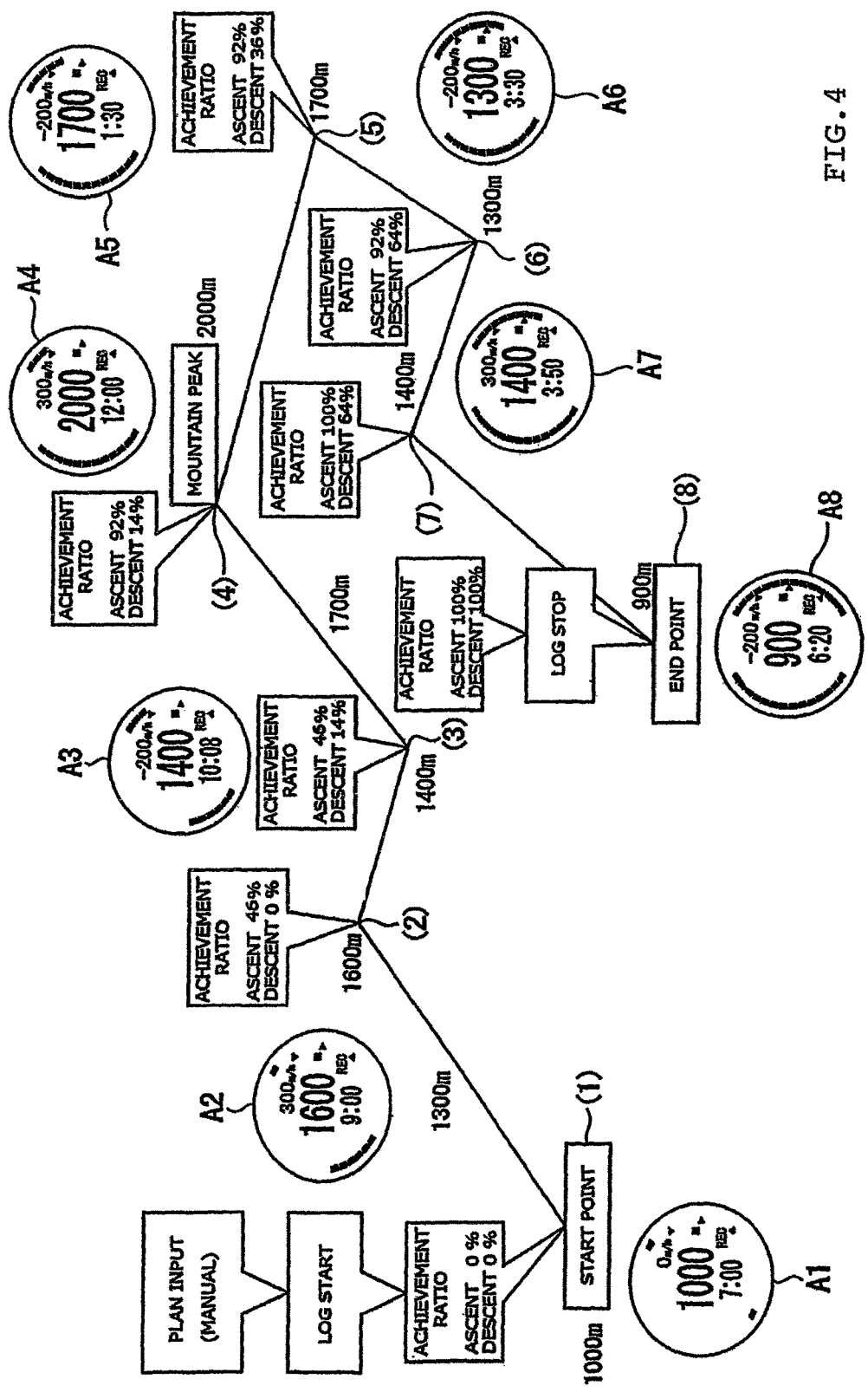
FIG. 4 is a view for describing an operation of the electronic timepiece according to the first embodiment of the present invention.
Figure 5:
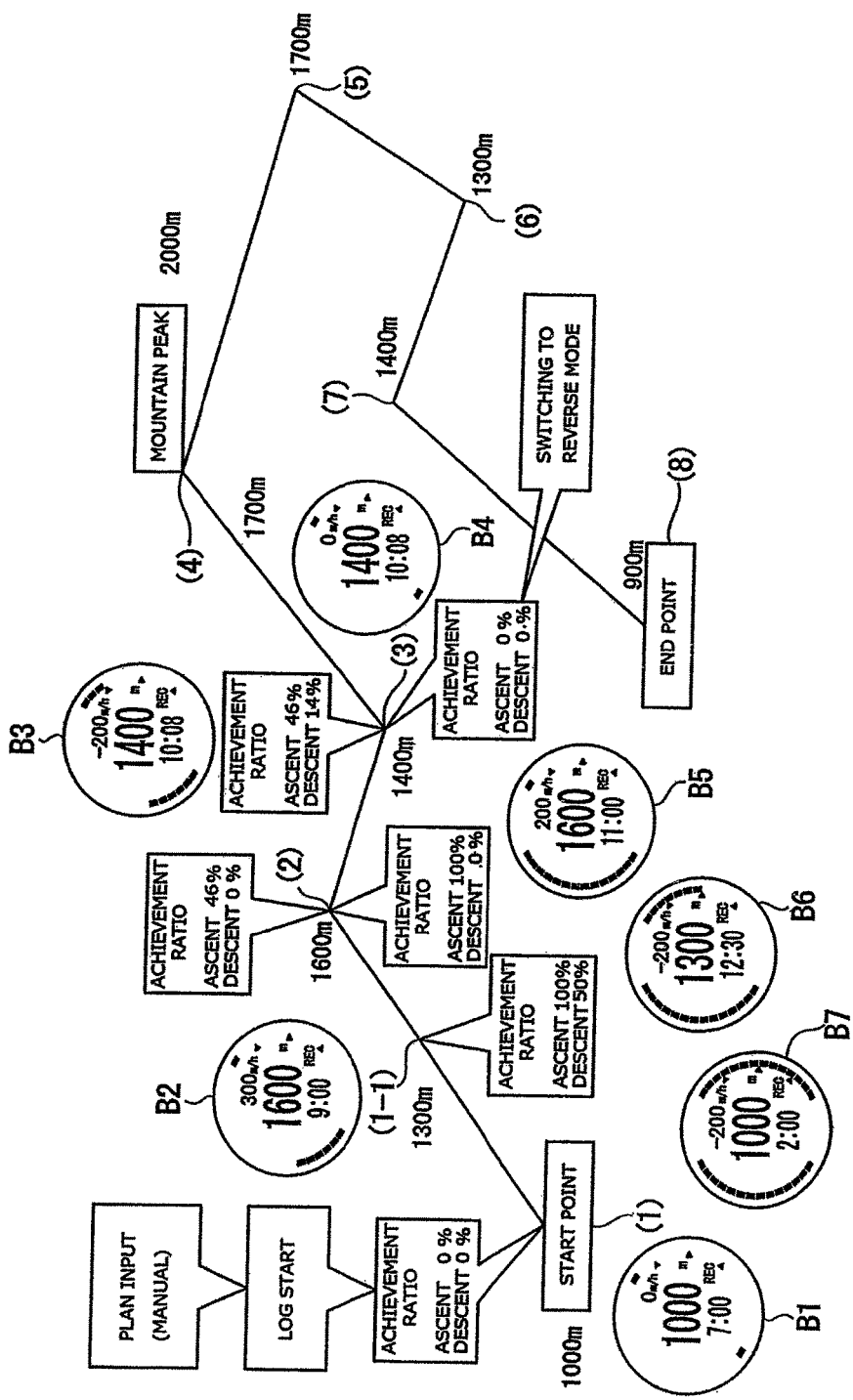
FIG. 5 is a view for describing an operation of the electronic timepiece according to the first embodiment of the present invention.

Next, an operation of the electronic timepiece 100 will be described with reference to a specific example. FIGS. 4 and 5 are views for describing the operation of the electronic timepiece 100 according to the present embodiment. Planning illustrated in FIGS. 4 and 5 represents a mountain climbing plan, in which after starting a mountain climbing from a mountain climbing start point (1), a user arrives at a mountain descent end point (8) by way of a mountain peak (4). The mountain climbing start point (1) is a starting point, and the mountain descent end point (8) is a goal point. The mountain climbing plan includes a start altitude, an end altitude, a total ascent altitude, and a total descent altitude. The start altitude is an altitude at the starting point. The end altitude is an altitude at the goal point. The total ascent altitude represents a total value of an altitude at which the user travels during an ascent, and is the ascent integrated altitude plan value. The total descent altitude represents a total value of an altitude at which the user travels during a descent, and is the descent integrated altitude plan value. In this example, the start altitude is an altitude of 1,000 m at the mountain climbing start point. The end altitude is an altitude of 900 in at the mountain descent end point. The total ascent altitude is 1,300 m. The total descent altitude is 1,400 m.

First, the user inputs the mountain climbing plan through the key input means 104. If the key input means 104 receives the input of the mountain climbing plan, the CPU 101 writes the input mountain climbing plan on the RAM 110. In this case, the CPU 101 sets the total ascent altitude as the ascent integrated altitude plan value, and sets the total descent altitude as the descent integrated altitude plan value. Thereafter, at the mountain climbing start point (1), the user inputs the mountain climbing log start to the key input means 104. If the key input means 104 receives the input of the mountain climbing log start, the CPU 101 performs the process illustrated in FIG. 3, and displays the achievement ratio.

In this example, the user inputs the mountain climbing plan at the mountain climbing start point (1). However, without being limited thereto, the user may input the mountain climbing plan before starting the mountain climbing. For example, the user may input the mountain climbing plan at home the day before.

FIG. 4 illustrates an example in which the user arrives at the mountain descent end point (8) in accordance with the mountain climbing plan. Both the ascent achievement ratio and the descent achievement ratio at the mountain climbing start point (1) represent 0%. At the mountain climbing start point (1), the CPU 101 causes the display unit 105 to display a display A1. The ascent speed on the display A1 is 0 m/h. The altitude is 1,000 m. The time is 7:00. Both the indicator for indicating the ascent achievement ratio and the indicator for indicating the descent achievement ratio on the display A1 indicate 0%.

Subsequently, if the user arrives at a point (2) whose altitude is 1,600 m, the CPU 101 calculates the ascent achievement ratio of 46% and the descent achievement ratio of 0%, and causes the display unit 105 to display a display A2. The ascent speed on the display A2 is 300 m/h. The altitude is 1,600 m. The time is 9:00. The indicator for indicating the ascent achievement ratio on the display A2 indicates 46%. The indicator for indicating the descent achievement ratio indicates 0%.

Subsequently, if the user arrives at a point (3) whose altitude is 1,400 m, the CPU 101 calculates the ascent achievement ratio of 46% and the descent achievement ratio of 14%, and causes the display unit 105 to display a display A3. The ascent speed on the display A3 is −200 m/h. The altitude is 1,400 m. The time is 10:08. The indicator for indicating the ascent achievement ratio on the display A3 indicates 46%. The indicator for indicating the descent achievement ratio indicates 14%.

Subsequently, if the user arrives at the mountain peak (4) whose altitude is 2,000 m, the CPU 101 calculates the ascent achievement ratio of 92% and the descent achievement ratio of 14%, and causes the display unit 105 to display a display A4. The ascent speed on the display A4 is 300 m/h. The altitude is 2,000 m. The time is 12:00. The indicator for indicating the ascent achievement ratio on the display A4 indicates 92%. The indicator for indicating the descent achievement ratio indicates 14%.

Subsequently, if the user arrives at a point (5) whose altitude is 1,700 m, the CPU 101 calculates the ascent achievement ratio of 92% and the descent achievement ratio of 36%, and causes the display unit 105 to display a display A5. The ascent speed on the display A5 is −200 m/h. The altitude is 1,700 m. The time is 1:30. The indicator for indicating the ascent achievement ratio on the display A5 indicates 92%. The indicator for indicating the descent achievement ratio indicates 36%.

Subsequently, if the user arrives at a point (6) whose altitude is 1,300 m, the CPU 101 calculates the ascent achievement ratio of 92% and the descent achievement ratio of 64%, and causes the display unit 105 to display a display A6. The ascent speed on the display A6 is −200 m/h. The altitude is 1,300 m. The time is 3:30. The indicator for indicating the ascent achievement ratio on the display A6 indicates 92%. The indicator for indicating the descent achievement ratio indicates 64%.

Subsequently, if the user arrives at a point (7) whose altitude is 1,400 m, the CPU 101 calculates the ascent achievement ratio of 100% and the descent achievement ratio of 64%, and causes the display unit 105 to display a display A7. The ascent speed on the display A7 is 300 m/h. The altitude is 1,400 m. The time is 3:50. The indicator for indicating the ascent achievement ratio on the display A7 indicates 100%, The indicator for indicating the descent achievement ratio indicates 64%.

Subsequently, if the user arrives at the mountain descent endpoint (8) whose altitude is 900 m, the CPU 101 calculates the ascent achievement ratio of 100% and the descent achievement ratio of 100%, and causes the display unit 105 to display a display A8. The ascent speed on the display A8 is −200 m/h. The altitude is 900 m. The time is 6:20. The indicator for indicating the ascent achievement ratio on the display A8 indicates 100%. The indicator for indicating the descent achievement ratio indicates 100%.

As described above, when the user arrives at the mountain descent end point (8) from the mountain climbing start point (1), the electronic timepiece 100 displays the ascent speed, the altitude, the time, the indicator for indicating the ascent achievement ratio, and the indicator for indicating the descent achievement ratio. In this manner, the user can recognize the ascent/descent achievement ratio (the ascent achievement ratio and the descent achievement ratio) with respect to the plan.

FIG. 5 illustrates an example in which the user returns at an intermediate point (3) of the mountain climbing plan. Displays B1 to B3 from the mountain climbing start point (1) to the point (3) are the same as the above-described displays A1 to A3, and thus, description thereof will be omitted.

If the user determines to return at the point (3), the user performs an input for switching to a reverse mode on the key input means 104. If the key input means 104 receives the input for switching to the reverse mode (indicating that the user returns), the CPU 101 sets the calculated ascent integrated altitude value of 600 m as the descent integrated altitude plan value, and sets the calculated descent integrated altitude value of 200 m as the ascent integrated altitude plan value. The CPU 101 initializes the ascent integrated altitude value, the descent integrated altitude value, the ascent achievement ratio, and the descent achievement ratio to zero. Then, the CPU 101 causes the display unit 105 to display a display B4. The ascent speed on the display B4 is 0 m/h. The altitude is 1,400 m. The time is 10:08. The indicator for indicating the ascent achievement ratio on the display B4 indicates 0%. The indicator for indicating the descent achievement ratio indicates 0%. That is, based on the mountain climbing plan in which the return point (3) is set as the starting point, the mountain climbing start point (1) is set as the goal point, the ascent integrated altitude value is set as the descent integrated altitude plan value, and the descent integrated altitude value is set as the ascent integrated altitude plan value, the CPU 101 recalculates and displays the ascent achievement ratio and the descent achievement ratio.

Subsequently, if the user arrives at the point (2) whose altitude is 1,600 m, the CPU 101 calculates the ascent achievement ratio of 100% and the descent achievement ratio of 0%, and causes the display unit 105 to display a display B5. The ascent speed on the display B5 is 200 m/h. The altitude is 1,600 m. The time is 11:00. The indicator for indicating the ascent achievement ratio on the display B5 indicates 100%. The indicator for indicating the descent achievement ratio indicates 0%.

Subsequently, if the user arrives at a point (1-1) whose altitude is 1,300 m, the CPU 101 calculates the ascent achievement ratio of 100% and the descent achievement ratio of 50%, and causes the display unit 105 to display a display B6. The ascent speed on the display B6 is −200 m/h. The altitude is 1,300 m. The time is 12:30. The indicator for indicating the ascent achievement ratio on the display B6 indicates 100%. The indicator for indicating the descent achievement ratio indicates 50%.

Subsequently, if the user arrives at the mountain climbing start point (1) whose altitude is 1,000 m, the CPU 101 calculates the ascent achievement ratio of 100% and the descent achievement ratio of 100%, and causes the display unit 105 to display a display B7. The ascent speed on the display B7 is −200 m/h. The altitude is 1,000 m. The time is 2:00. The indicator for indicating the ascent achievement ratio on the display B7 indicates 100%. The indicator for indicating the descent achievement ratio indicates 100%.

As described above, if the input for switching to the reverse mode is received, the electronic timepiece 100 calculates the ascent achievement ratio and the descent achievement ratio by setting the ascent integrated altitude value obtained so far as the descent integrated altitude plan value and setting the descent integrated altitude value obtained so far as the ascent integrated altitude plan value. In this manner, the user can recognize the ascent achievement ratio and the descent achievement ratio from the return point (3) to the mountain climbing start point (1) which is the starting point.

As described above, according to the present embodiment, the electronic timepiece 100 includes the altitude measurement unit 108 that measures the altitude, the CPU 101 that causes the display unit 105 to display the ascent achievement ratio and the descent achievement ratio after calculating the ascent integrated altitude value obtained by integrating the altitude variation amount during the ascent and the descent integrated altitude value obtained by integrating the altitude variation amount during the descent, based on the altitude measured by the altitude measurement unit 108, and calculating the ascent achievement ratio which is the achievement ratio of the ascent integrated altitude value with respect to the ascent integrated altitude plan value and the descent achievement ratio which is the achievement ratio of the descent integrated altitude value with respect to the descent integrated altitude plan value, and the RAM 110 that stores the ascent integrated altitude plan value and the descent integrated altitude plan value.

In this manner, the user does not have to perform calculation by himself or by herself, and can easily recognize the ascent/descent achievement ratio with respect to the total plan, thereby allowing the user to feel improved convenience. Accordingly, referring to the achievement ratio, the user can immediately determine whether to continue or stop the mountain climbing leading to ensure safety of the user. The user can concurrently recognize the ascent achievement ratio and the descent achievement ratio.

If the key input means 104 receives the predetermined input which is an instruction to perform switching to the reverse mode, the CPU 101 calculates the ascent achievement ratio and the descent achievement ratio after setting the calculated ascent integrated altitude value as the descent integrated altitude plan value and setting the calculated descent integrated altitude value as the ascent integrated altitude plan value. In this manner, even in a case where the user intermediately stops the mountain climbing and returns, the user can easily recognize the ascent achievement ratio and the descent achievement ratio up to the starting point which is the return destination.

The CPU 101 displays the ascent speed, the altitude, and the current time together with the ascent achievement ratio and the descent achievement ratio. This enables the user to easily recognize the ascent speed, the altitude, and the current time in addition to the ascent achievement ratio and the descent achievement ratio. For example, the user can recognize the current position by concurrently viewing the altitude and the achievement ratio. The user can determine whether or not the user is in a proper pace with respect to the mountain climbing plan by concurrently viewing the ascent speed and the achievement ratio. The user can immediately determine a status of the mountain climbing plan by concurrently viewing the current time and the achievement ratio.

The CPU 101 displays the ascent achievement ratio and the descent achievement ratio by using the indicator whose size can be visually identified based on the display area. This enables the user to more intuitively recognize the ascent achievement ratio and the descent achievement ratio.

Second Embodiment

Next, a second embodiment according to the present invention will be described. A configuration of the electronic timepiece 100 according to the present embodiment is the same as that according to the first embodiment, and thus, description thereof will be omitted. The present embodiment and the first embodiment respectively have different methods of calculating the ascent achievement ratio and the descent achievement ratio during the reverse mode.

Specifically, if the key input means 104 receives a predetermined input indicating that the user returns, the CPU 101 adds the previously calculated ascent integrated altitude value and the previously calculated descent integrated altitude value, and sets the added value as the ascent integrated altitude plan value and the descent integrated altitude plan value. For example, the CPU 101 adds an absolute value of the ascent integrated altitude value and an absolute value of the descent integrated altitude value which are obtained when the predetermined input is received, and writes and stores the added value on the RAM 110 as the ascent integrated altitude plan value and the descent integrated altitude plan value. Then, the CPU 101 calculates the ascent achievement ratio which is the achievement ratio of the ascent integrated altitude value with respect to the set ascent integrated altitude plan value and the descent achievement ratio which is the achievement ratio of the descent integrated altitude value with respect to the set descent integrated altitude plan value, and causes the display unit 105 to display both of these.

Figure 6:
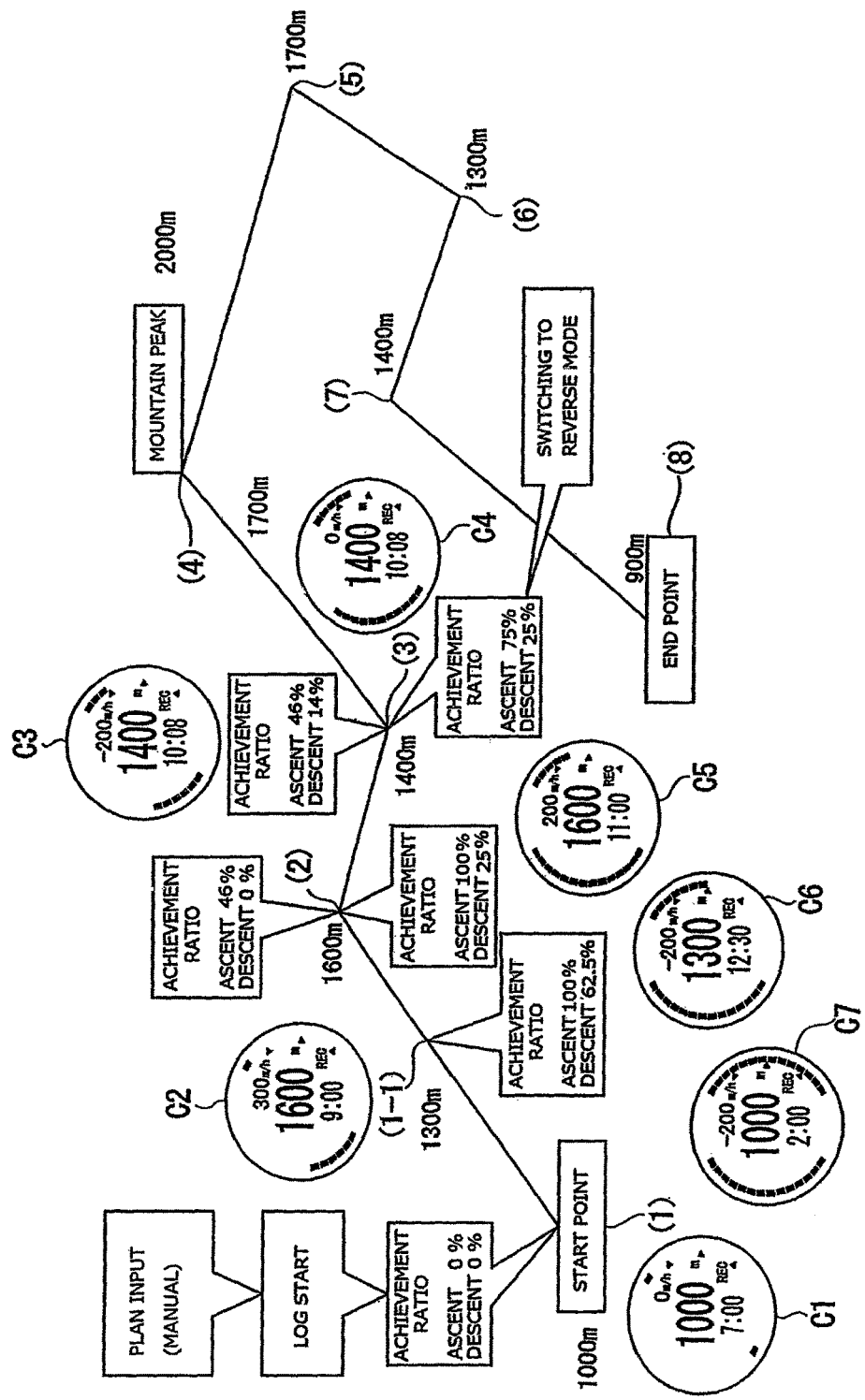
FIG. 6 is a view for describing an operation of an electronic timepiece according to a second embodiment of the present invention.
Figure 7:
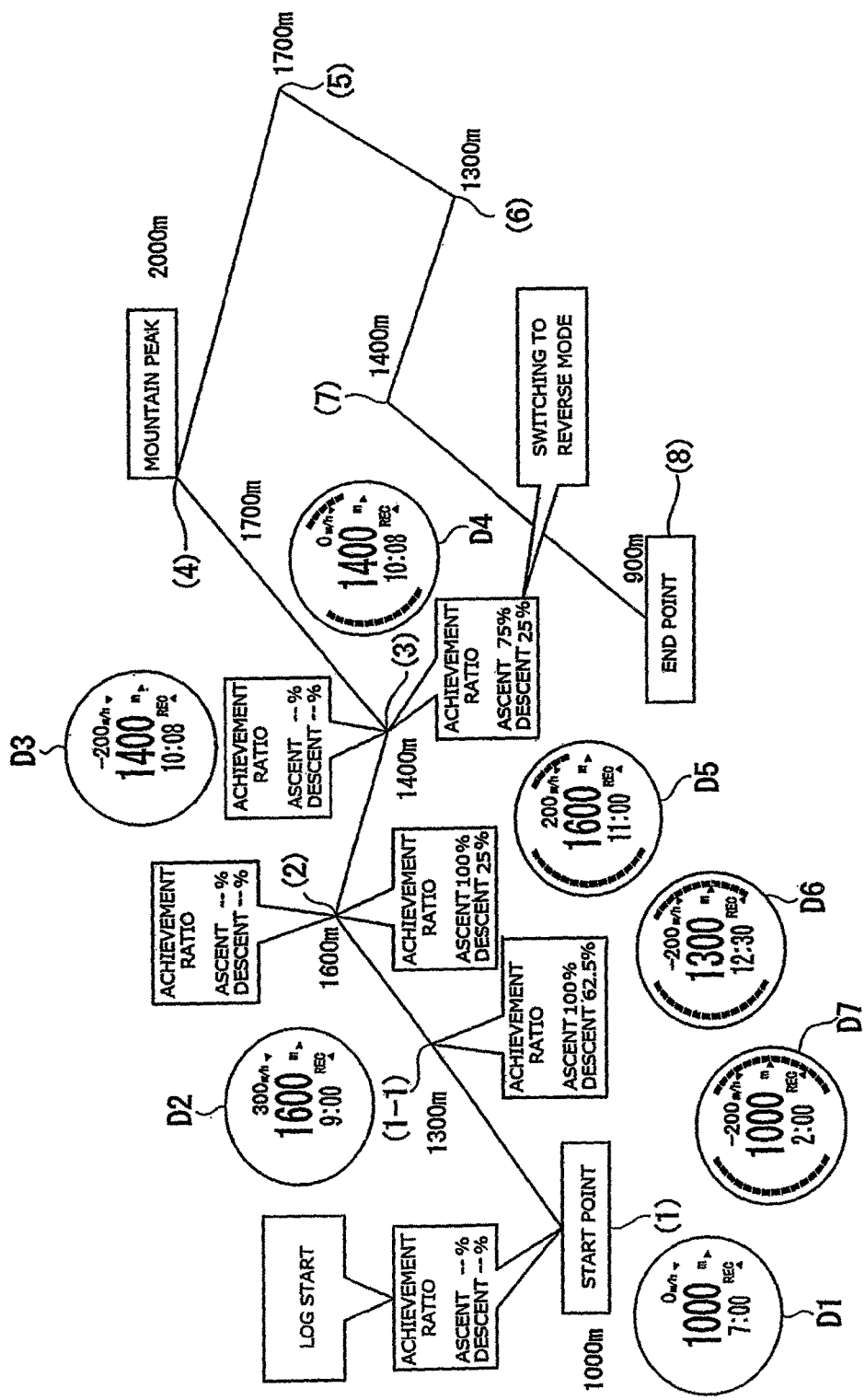
FIG. 7 is a view for describing an operation of the electronic timepiece according to the second embodiment of the present invention.

Next, an operation of the electronic timepiece 100 will be described with reference to a specific example. FIGS. 6 and 7 are views for describing the operation of the electronic timepiece 100 according to the present embodiment. FIGS. 6 and 7 illustrate an example in which a user returns at the intermediate point (3) in the mountain climbing plan. Planning illustrated in FIG. 6 is the same as that according to the first embodiment, and thus, description thereof will be omitted. Displays C1 to C3 from the mountain climbing start point (1) to the point (3) are the same as the above-described displays A1 to A3, and thus, description thereof will be omitted.

If the user determines to return at the point (3), the user performs an input for switching to a reverse mode on the key input means 104. If the key input means 104 receives the input for switching to the reverse mode (indicating that the user returns), the CPU 101 adds the calculated ascent integrated altitude value of 600 m and the calculated descent integrated altitude value of 200 m, and sets the added value of 800 m as the ascent integrated altitude plan value and the descent integrated altitude plan value. Thereafter, the CPU 101 calculates the ascent integrated altitude value of 600 m/the set ascent integrated altitude plan value of 800 m×100=the ascent achievement ratio of 75% and the descent integrated altitude value of 200 m/the set descent integrated altitude plan value of 800 m×100=the descent achievement ratio of 25%.

Then, the CPU 101 causes the display unit 105 to display a display C4. The ascent speed on the display C4 is 0 m/h. The altitude is 1,400 m. The time is 10:08. The indicator for indicating the ascent achievement ratio on the display C4 indicates 75%. The indicator for indicating the descent achievement ratio indicates 25%. That is, based on the mountain climbing plan in which the mountain climbing start point (1) is set as the goal point, and a value obtained by adding the calculated ascent integrated altitude value and the calculated descent integrated altitude value is set as the ascent integrated altitude plan value and the descent integrated altitude plan value, the CPU 101 recalculates and displays the ascent achievement ratio and the descent achievement ratio.

Subsequently, if the user arrives at the point (2) whose altitude is 1,600 m, the CPU 101 calculates the ascent achievement ratio of 100% and the descent achievement ratio of 25%, and causes the display unit 105 to display a display C5. The ascent speed on the display C5 is 200 m/h. The altitude is 1,600 in. The time is 11:00. The indicator for indicating the ascent achievement ratio on the display C5 indicates 100%. The indicator for indicating the descent achievement ratio indicates 25%.

Subsequently, if the user arrives at the point (1-1) whose altitude is 1,300 m, the CPU 101 calculates the ascent achievement ratio of 100% and the descent achievement ratio of 62.5%, and causes the display unit 105 to display a display C6. The ascent speed on the display C6 is −200 m/h. The altitude is 1,300 m. The time is 12:30. The indicator for indicating the ascent achievement ratio on the display C6 indicates 100%. The indicator for indicating the descent achievement ratio indicates 62.5%.

Subsequently, if the user arrives at the mountain climbing start point (1) whose altitude is 1,000 m, the CPU 101 calculates the ascent achievement ratio of 100% and the descent achievement ratio of 100%, and causes the display unit 105 to display a display C7. The ascent speed on the display C7 is −200 m/h. The altitude is 1,000 in. The time is 2:00. The indicator for indicating the ascent achievement ratio on the display C7 indicates 100%. The indicator for indicating the descent achievement ratio indicates 100%.

As described above, if the input for switching to the reverse mode is received, the electronic timepiece 100 calculates the ascent achievement ratio and the descent achievement ratio by setting a value obtained by adding the ascent integrated altitude value so far and the descent integrated altitude value so far as the ascent integrated altitude plan value and the descent integrated altitude plan value. In this manner, the user can recognize the ascent achievement ratio and the descent achievement ratio from the return point (3) to the mountain climbing start point (1) which is the starting point.

FIG. 7 illustrates an example in which the mountain climbing plan is not set (no planning). Both the indicator for indicating the ascent achievement ratio and the indicator for indicating the descent achievement ratio in displays D1 to D3 from the mountain climbing start point (1) to the point (3) are not displayed. That is, since the mountain climbing plan is not set, the CPU 101 does not cause the display unit 105 to display the ascent achievement ratio and the descent achievement ratio. Other displays of the displays D1 to D3 are the same as those of the above-described displays C1 to C3, and thus, description thereof will be omitted. Displays D4 to D7 when the user returns from the point (3) to the mountain climbing start point (1) are the same as the above-described displays C4 to C7, and thus, description thereof will be omitted.

As described above, even in a case where the mountain climbing plan is not set (the ascent integrated altitude plan value and the descent integrated altitude plan value are not stored in the RAM 110), if the input for switching to the reverse mode is received, the electronic timepiece 100 calculates the ascent achievement ratio and the descent achievement ratio by setting a value obtained by adding the ascent integrated altitude value so far and the descent integrated altitude value so far as the ascent integrated altitude plan value and the descent integrated altitude plan value. In this manner, even in a case where the mountain climbing plan is not set, the user can recognize the ascent achievement ratio and the descent achievement ratio from the return point (3) to the mountain climbing start point (1) which is the starting point.

Without being limited to this example, the electronic timepiece 100 according to the first embodiment also sets the previously calculated ascent integrated altitude value as the descent integrated altitude plan value, and also sets the previously calculated descent integrated altitude value as the ascent integrated altitude plan value. Accordingly, even in a case where the mountain climbing plan is not set, the electronic timepiece 100 can display the ascent achievement ratio and the descent achievement ratio during the reverse mode.

As described above, according to the present embodiment, if the key input means 104 receives the predetermined input, the CPU 101 of the electronic timepiece 100, causes the RAM 110 to store the value obtained by adding the absolute value of the ascent integrated altitude value and the absolute value of the descent integrated altitude value which are obtained when the predetermined input is received, as the ascent integrated altitude plan value and the descent integrated altitude plan value. Based on the ascent integrated altitude plan value stored in the RAM 110, the CPU 101 calculates the ascent achievement ratio. Based on the descent integrated altitude plan value stored in the RAM 110, the CPU 101 calculates the descent achievement ratio.

In this manner, even in a case where the user intermediately stops the mountain climbing and returns, the user can easily recognize the ascent achievement ratio and the descent achievement ratio up to the starting point which is the return destination. Even in a case where the mountain climbing plan is not set (the ascent integrated altitude plan value and the descent integrated altitude plan value are not stored in the RAM 110), the user can easily recognize the ascent achievement ratio and the descent achievement ratio from the return point to the starting point.

Third Embodiment

Next, a third embodiment according to the present invention will be described. A configuration of the electronic timepiece 100 according to the present embodiment is the same as that according to the first embodiment, and thus, description thereof will be omitted. The present embodiment and the first embodiment respectively have different methods of calculating the ascent achievement ratio and the descent achievement ratio during the reverse mode.

Specifically, if the key input means 104 receives a predetermined input indicating that the user returns, the CPU 101 newly starts to measure the ascent integrated altitude value and the descent integrated altitude value from zero. Then, the CPU 101 calculates the ascent integrated altitude value by deducting the newly calculated descent integrated altitude value (obtained after the key input means 104 receives the input indicating that a user returns) from the previously calculated ascent integrated altitude value (obtained when the key input means 104 receives the input indicating that the user returns). The CPU 101 calculates the descent integrated altitude value by deducting the newly calculated ascent integrated altitude value (obtained after the key input means 104 receives the input indicating that the user returns) from the previously calculated descent integrated altitude value (obtained when the key input means 104 receives the input indicating that the user returns). Then, the CPU 101 calculates the ascent achievement ratio which is the achievement ratio of the ascent integrated altitude value with respect to the ascent integrated altitude plan value and the descent achievement ratio which is the achievement ratio of the descent integrated altitude value with respect to the descent integrated altitude plan value, and causes the display unit 105 to display both of these.

Figure 8:
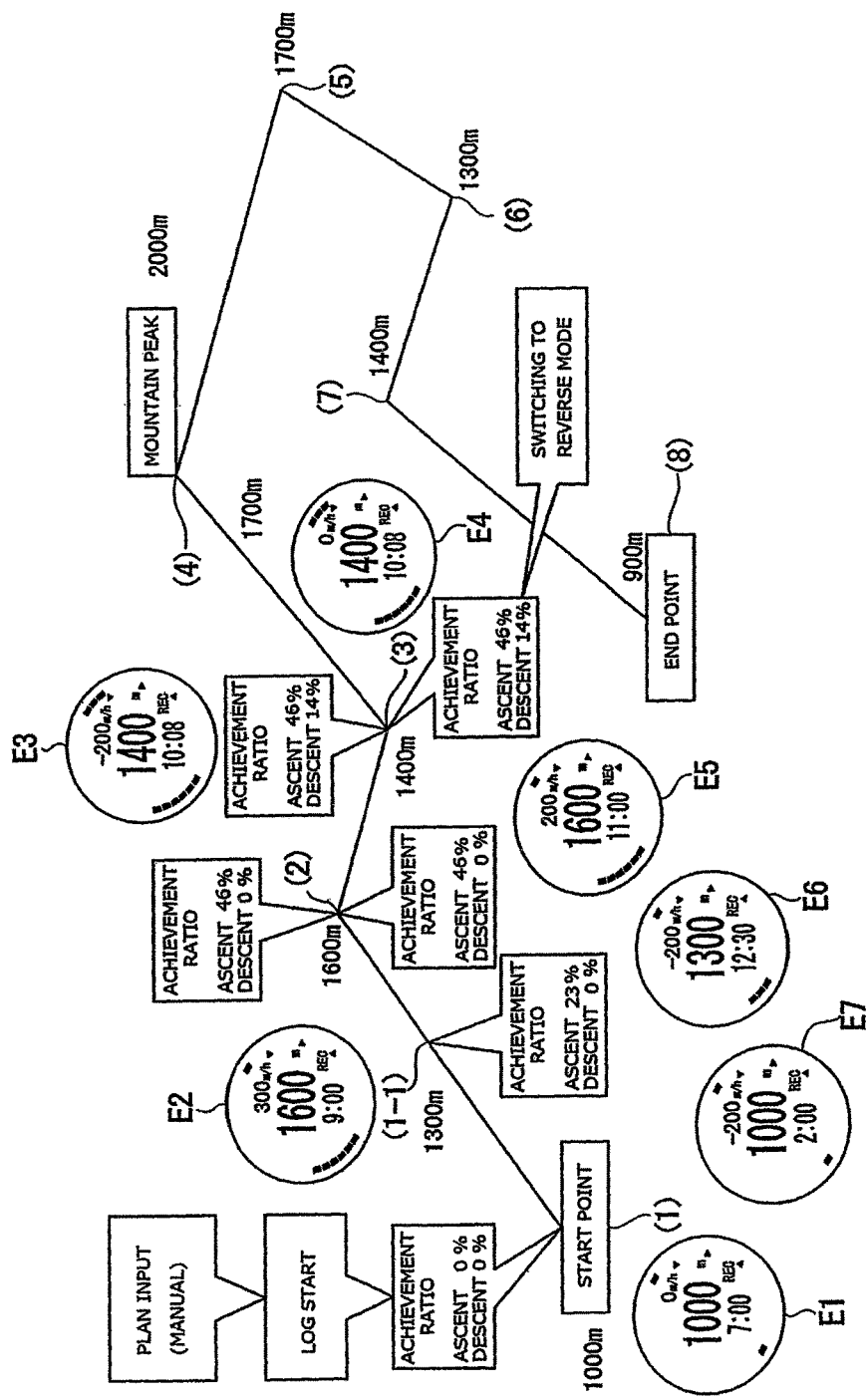
FIG. 8 is a view for describing an operation of an electronic timepiece according to a third embodiment of the present invention.

Next, an operation of the electronic timepiece 100 will be described with reference to a specific example. FIG. 8 is a view for describing the operation of the electronic timepiece 100 according to the present embodiment. FIG. 8 illustrates an example in which a user returns at the intermediate point (3) in the mountain climbing plan. Planning illustrated in FIG. 8 is the same as that according to the first embodiment, and thus, description thereof will be omitted. Displays E1 to E3 from the mountain climbing start point (1) to the point (3) are the same as the above-described displays A1 to A3, and thus, description thereof will be omitted.

If the user determines to return at the point (3), the user performs an input for switching to a reverse mode on the key input means 104. If the key input means 104 receives the input for switching to the reverse mode (indicating that the user returns), the CPU 101 newly starts to measure the ascent integrated altitude value and the descent integrated altitude value from zero. The CPU 101 initializes the ascent speed into 0 m/h.

Then, the CPU 101 causes the display unit 105 to display a display E4. The ascent speed on the display E4 is 0 m/h. The altitude is 1,400 m. The time is 10:08. The indicator for indicating the ascent achievement ratio on the display E4 indicates 46%. The indicator for indicating the descent achievement ratio indicates 14%.

Subsequently, if the user arrives at the point (2) whose altitude is 1,600 m, the CPU 101 calculates the ascent achievement ratio of 46% and the descent achievement ratio of 0%, and causes the display unit 105 to display a display E5. Specifically, the CPU 101 calculates the ascent integrated altitude value of 600 m at the point (3)−the newly calculated descent integrated altitude value of 0 m/the ascent integrated altitude plan value of 1,300 m×100=the ascent achievement ratio of 46% and the descent integrated altitude value of 200 m at the point (3)−the newly calculated ascent integrated altitude value of 200 m/the descent integrated altitude plan value of 1,400 m×100=the descent achievement ratio of 0%. The ascent speed on the display E5 is 200 m/h. The altitude is 1,600 m. The time is 11:00. The indicator for indicating the ascent achievement ratio on the display E5 indicates 46%. The indicator for indicating the descent achievement ratio indicates 0%.

Subsequently, if the user arrives at the point (1-1) whose altitude is 1,300 m, the CPU 101 calculates the ascent achievement ratio of 23% and the descent achievement ratio of 0%, and causes the display unit 105 to display a display E6. Specifically, the CPU 101 calculates the ascent integrated altitude value of 600 m at the point (3)−the newly calculated descent integrated altitude value of 300 m/the ascent integrated altitude plan value of 1,300 m×100=the ascent achievement ratio of 23% and the descent integrated altitude value of 200 m at the point (3)−the newly calculated ascent integrated altitude value of 200 m/the descent integrated altitude plan value Of 1,400 m×100=the descent achievement ratio of 0%. The ascent speed on the display E6 is −200 m/h. The altitude is 1,300 m. The time is 12:30. The indicator for indicating the ascent achievement ratio on the display E6 indicates 23%. The indicator for indicating the descent achievement ratio indicates 0%.

Subsequently, if the user arrives at the mountain climbing start point (1) whose altitude is 1,000 m, the CPU 101 calculates the ascent achievement ratio of 0% and the descent achievement ratio of 0%, and causes the display unit 105 to display a display E7. The ascent speed on the display E7 is −200 m/h. The altitude is 1,000 m. The time is 2:00. The indicator for indicating the ascent achievement ratio on the display E7 indicates 0%. The indicator for indicating the descent achievement ratio indicates 0%.

As described above, if the input for switching to the reverse mode is received, the electronic timepiece 100 calculates the ascent integrated altitude value by deducting the newly calculated descent integrated altitude value from the ascent integrated altitude value obtained so far, and calculates the descent integrated altitude value by deducting the newly calculated ascent integrated altitude value from the descent integrated altitude value obtained so far. Accordingly, the ascent achievement ratio and the descent achievement ratio which are displayed by the electronic timepiece 100 become lower as the user moves closer to the starting point from when the user returns. This enables the user to more intuitively recognize the ascent achievement ratio and the descent achievement ratio from the return point (3) to the mountain climbing start point (1) which is the starting point.

As described above, according to the present embodiment, if the key input means 104 receives the predetermined input, the CPU 101 of the electronic timepiece 100 calculates the ascent integrated altitude value by deducting an absolute value of the descent integrated altitude value obtained after the predetermined input is received, from an absolute value of the ascent integrated altitude value obtained when the key input means 104 receives the predetermined input, and calculates the descent integrated altitude value by deducting an absolute value of the ascent integrated altitude value obtained after the predetermined input is received, from an absolute value of the descent integrated altitude value obtained when the predetermined input is received. In this manner, even in a case where the user intermediately stops the mountain climbing and returns, the user can easily recognize the ascent achievement ratio and the descent achievement ratio.

Functions of the respective units included in the electronic timepiece 100 according to the above-described embodiments may be entirely or partially realized by executing a program in such a way that the program for realizing the functions is recorded on a computer-readable recording medium and the program recorded on the recording medium is read by a computer system. The "computer system" described herein includes an OS or hardware such as peripheral devices.

The "computer-readable recording medium" means a portable medium such as a flexible disk, a magneto-optical disk, a ROM, and a CD-ROM or a storage unit such as a hard disk incorporated into the computer system. Furthermore, the "computer-readable recording medium" may include those which dynamically hold the program within a short period of time, like a communication line in a case where the program is transmitted via a network such as the Internet and a communication channel such as a telephone line, or those which hold the program for a fixed period of time like a volatile memory inside the computer system functioning as a server or a client in that case. A configuration may also be adopted in which the above-described functions may be partially realized by the program or may be realized in combination with a program which is previously recorded in the computer system.

Hitherto, the embodiments according to the present invention have been described. However, without being limited to the above-described embodiments, the present invention can be modified in various ways within the scope not departing from the gist of the present invention.

For example, according to the above-described embodiments, the CPU 101 calculates the ascent achievement ratio and the descent achievement ratio, and causes the display unit 105 to display both of these. However, without being limited thereto, the CPU 101 may calculate and display only the ascent achievement ratio.

According to the above-described embodiments, the CPU 101 displays the ascent achievement ratio and the descent achievement ratio by using the respective indicators. However, without being limited thereto, the CPU 101 may display the ascent achievement ratio and the descent achievement ratio by using other display means such as numbers, for example.

According to the above-described embodiments, the CPU 101 causes the display unit 105 to display the ascent speed, the altitude, and the time together with the ascent achievement ratio and the descent achievement ratio. However, without being limited thereto, the CPU 101 may cause the display unit 105 to display at least one of the ascent speed, the altitude, and the time together with the ascent achievement ratio and the descent achievement ratio.

According to the above-described embodiments, the key input means 104 inputs the planning. However, without being limited thereto, for example, the planning may be input from other devices (for example, a smartphone or a tablet terminal) via the radio communication means 109.

According to the above-described embodiments, the electronic timepiece 100 causes the key input means 104 to input the planning of the mountain climbing plan. However, without being limited thereto, the electronic timepiece 100 may create the mountain climbing plan, based on the ascent integrated altitude value and the descent integrated altitude value which are measured in the past. For example, after the mountain climbing is completed, the CPU 101 may write and store the ascent integrated altitude value and the descent integrated altitude value which are obtained from the starting point to the goal point, on the RAM 110 as a mountain climbing record. Then, the CPU 101 may create the mountain climbing plan, based on the mountain climbing record recorded in the RAM 110 when the mountain climbing plan is created. Specifically, the CPU 101 may set the ascent integrated altitude value present in the mountain climbing record as the ascent integrated altitude plan value, and may set the descent integrated altitude value present in the mountain climbing record as the descent integrated altitude plan value. Alternatively, other devices may create the mountain climbing plan, based on the ascent integrated altitude value and the descent integrated altitude value which are measured in the past.

According to the above-described embodiments, the electronic timepiece 100 displays the indicator for indicating the achievement ratio, for example, in block units of every 5% or 10%. The electronic timepiece 100 may change the display method before and after the mode is switched to the reverse mode. Specifically, if the key input means 104 receives the predetermined input for switching to the reverse mode, the CPU 101 may change a method of displaying the achievement ratio. That is, before the mode is switched to the reverse mode, the electronic timepiece 100 may display a block display of the indicator by rounding up the calculated achievement ratio. For example, in a case where the indicator is displayed in the block of every 5%, when the achievement ratio is 46%, the electronic timepiece 100 may display the achievement ratio by using 10 blocks (50/5=10). On the other hand, after the mode is switched to the reverse mode, the electronic timepiece 100 may display the block display of the indicator by rounding down the calculated achievement ratio. For example, in a case where the indicator is displayed in the block of every 5%, when the achievement ratio is 46%, the electronic timepiece 100 may display the achievement ratio by using 9 blocks (45/5=9). In this manner, when the user aims to reach the mountain peak (before the reverse mode) and returns (reverse mode), the user can actually feel a change in the indicator display, thereby allowing the user to feel improved convenience as a user interface.

In the above-described embodiments, the electronic timepiece 100 functioning as an electronic device has been described as an example. However, without being limited thereto, the electronic device may be other devices such as a smartphone provided with an altimeter and an altitude measurement function.

What is claimed is:

1. An altimeter comprising:
   a display unit;
   an altitude measurement unit that measures an altitude;
   an altitude integration unit that calculates an ascent integrated altitude value obtained by integrating an altitude variation amount during an ascent, based on the altitude measured by the altitude measurement unit;
   a storage unit that stores an ascent integrated altitude plan value which is a plan value of the ascent integrated altitude value;
   an achievement ratio calculation unit that calculates an ascent achievement ratio which is an achievement ratio of the ascent integrated altitude value with respect to the ascent integrated altitude plan value; and
   a display control unit that causes the display unit to display the ascent achievement ratio.

2. The altimeter according to claim 1,
   wherein the altitude integration unit calculates a descent integrated altitude value obtained by integrating an altitude variation amount during a descent, based on the altitude measured by the altitude measurement unit,
   wherein the storage unit stores a descent integrated altitude plan value which is a plan value of the descent integrated altitude value,
   wherein the achievement ratio calculation unit calculates a descent achievement ratio which is an achievement ratio of the descent integrated altitude value with respect to the descent integrated altitude plan value, and
   wherein the display control unit causes the display unit to display the descent achievement ratio.

3. The altimeter according to claim 1, further comprising:
   an input unit that receives an input,
   wherein if the input unit receives a predetermined input, the achievement ratio calculation unit sets the integrated altitude plan value, based on the integrated altitude value previously calculated by the altitude integration unit, and calculates the achievement ratio, based on the set integrated altitude plan value.

4. The altimeter according to claim 3,
   wherein the storage unit stores an absolute value of the ascent integrated altitude value obtained when the predetermined input is received, as the descent integrated altitude plan value,
   wherein the altitude integration unit calculates the descent integrated altitude value based on the altitude obtained when the predetermined input is received, and
   wherein the achievement ratio calculation unit calculates the descent achievement ratio which is an achievement ratio of the descent integrated altitude value with respect to the descent integrated altitude plan value.

5. The altimeter according to claim 2, further comprising:
   an input unit that receives an input,
   wherein if the input unit receives a predetermined input, the achievement ratio calculation unit causes the storage unit to store a value obtained by adding an absolute value of the ascent integrated altitude value and an absolute value of the descent integrated altitude value which are obtained when the predetermined input is received, as the ascent integrated altitude plan value and the descent integrated altitude plan value, calculates the ascent achievement ratio, based on the ascent integrated altitude plan value stored in the storage unit, and calculates the descent achievement ratio, based on the descent integrated altitude plan value stored in the storage unit.

6. The altimeter according to claim 2, further comprising:
   an input unit that receives an input,
   wherein if the input unit receives a predetermined input, the altitude integration unit calculates the ascent integrated altitude value by deducting an absolute value of the descent integrated altitude value obtained after the predetermined input is received from an absolute value of the ascent integrated altitude value obtained when the predetermined input is received, and calculates the descent integrated altitude value by deducting an absolute value of the ascent integrated altitude value obtained after the predetermined input is received from an absolute value of the descent integrated altitude value obtained when the predetermined input is received.

7. The altimeter according to claim 6,
wherein if the input unit receives the predetermined input, the display control unit changes a display method of the achievement ratio.

8. The altimeter according to claims 1,
wherein the display control unit causes the display unit to display at least one of altitude measured by the altitude measurement unit, speed based on the altitude variation amount, and a time, together with the achievement ratio.

9. The altimeter according to claim 2,
wherein the display control unit causes the display unit to display at least one of altitude measured by the altitude measurement unit, speed based on the altitude variation amount, and a time, together with the ascent achievement ratio and the descent achievement ratio.

10. The altimeter according to claim 1,
wherein the display control unit causes the display unit to display the achievement ratio which can visibly identify a size, based on a display area, and displays the achievement ratio so that a direction in which the display area for displaying the ascent achievement ratio increases and a direction in which the display area for displaying the descent achievement ratio increases are opposite to each other in the display unit.

11. The altimeter according to claim 1, further comprising:
a solar cell that generates power required for display of the display unit,
wherein the solar cell generates the power by using light received while the altitude measurement unit measures the altitude.

12. An electronic timepiece comprising:
the altimeter according to claims 1; and
a clocking function,
wherein the display control unit enables the display unit to display a time clocked by the clocking function.

13. A program that causes a computer of an altimeter to execute a process comprising:
an altitude measurement step of measuring an altitude;
an altitude integration step of calculating an ascent integrated altitude value obtained by integrating an altitude variation amount during an ascent, based on the altitude measured in the altitude measurement step;
an achievement ratio calculation step of calculating an ascent achievement ratio which is an achievement ratio of the ascent integrated altitude value with respect to an ascent integrated altitude plan value which is a plan value of the ascent integrated altitude value; and
a display control step of causing a display unit to display the ascent achievement ratio.

* * * * *